United States Patent

Tochikubo et al.

[11] Patent Number: 5,840,037
[45] Date of Patent: Nov. 24, 1998

[54] SPHYGMOMANOMETER

[75] Inventors: Osamu Tochikubo, Kanagawa; Shigehiro Ishizuka, Saitama, both of Japan

[73] Assignee: A & D Company, Limited, Tokyo, Japan

[21] Appl. No.: 793,336

[22] PCT Filed: Jun. 25, 1996

[86] PCT No.: PCT/JP96/01751

§ 371 Date: Jul. 22, 1997

§ 102(e) Date: Jul. 22, 1997

[87] PCT Pub. No.: WO97/49332

PCT Pub. Date: Dec. 31, 1997

[51] Int. Cl.⁶ .................................... A61B 05/00
[52] U.S. Cl. ............. 600/499; 600/479; 606/202
[58] Field of Search .................. 600/479, 485, 600/490, 493–7, 499, 500; 606/202

[56] References Cited

U.S. PATENT DOCUMENTS

| | | | |
|---|---|---|---|
| 3,633,567 | 1/1972 | Sarnoff | 600/499 |
| 4,653,506 | 3/1987 | Romanovskaya | 600/499 |
| 4,850,369 | 7/1989 | Yamasawa | 600/499 |
| 4,869,261 | 9/1989 | Penaz | 600/480 |
| 5,172,696 | 12/1992 | Souma | 600/480 |

FOREIGN PATENT DOCUMENTS

| | | |
|---|---|---|
| 60-60833 | 4/1985 | Japan . |
| 231734 | 2/1990 | Japan . |
| 535104 | 5/1993 | Japan . |
| 5329113 | 12/1993 | Japan . |

*Primary Examiner*—Robert L. Nasser
*Attorney, Agent, or Firm*—Sixbey Friedman Leedom & Ferguson; Thomas W. Cole

[57] ABSTRACT

The invention relates to a cuff for a sphygmomanometer, which is able to judge the maximum blood pressure and minimum blood pressure at a high accuracy. The cuff 10 comprises a bendably deformable hard curved plate 10a, an outside cloth 10b which surrounds the outer periphery of said curved plate 10a, an inside cloth 10c sewed to the outside cloth 10b so that the same surrounds the inner periphery of said curved plate 10a, an air bag 10d secured inside the inside cloth 10c, and an engaging fastener 10e sewed to the outer periphery of the outside cloth 10b. The air bag 10d is composed of a transparent bag member 10g in which reinforcing fabric 10f is incorporated in a latticed state. Each optical range sensor 12 is composed of a photocoupler 12a fixed at the outside of the bag member 10g and a reflection plate 12b fixed at the inside of the bag member 10g so as to be opposite to the photocoupler 12a. The photocoupler 12a has a light emitting diode and a phototransistor, whereby light emitted by the light emitting diode is reflected by the reflection plate 12b and is made incident into the phototransistor, and the output of the phototransistor may change in accordance with the distance between the photocoupler 12a and the reflection plate 12b.

5 Claims, 4 Drawing Sheets

SPHYGMOMANOMETER

FIELD OF THE INVENTION

The present invention relates to a cuff for a sphygmomanometer, and in particular relates to a cuff used for a closed type sphygmomanometer.

BACKGROUND OF THE INVENTION

A closed type electronic sphygmomanometer in which a cuff pressing the artery is wound on the upper arm of a patient is already known. For a tonometry hemadynamometry method with this kind of sphygmomanometer, although there are an oscillometric process, a Korotoff's sound method, an impedance method, etc., the oscillometric process has been mainly utilized in clinical applications. A sphygmomanometer in which a tonometry hemadynamometry method utilizing such an oscillometric process is employed is disclosed by, for example, Japanese Patent Publication No. 28637 of 1994.

A sphygmomanometer disclosed in the above publication is basically composed of a cuff having an air bag which is attached to the upper arm of a patient and presses the artery by supplying air therein, a pressure sensor which is able to detect the superposed pressure of the drop pressure and pulse pressure which change in said air bag of the cuff, a measuring section which converts the values detected by said pressure sensor into digital signals, a digital data processing section which is able to obtain the maximum and minimum blood pressure values of a patient by using the cuff pressure detection signals outputted by said measuring section as input data, and a display section which is able to display the maximum and minimum blood pressure values calculated by said digital data processing section.

With a sphygmomanometer constructed as described above, the maximum and minimum blood pressure values are judged by the digital data processing section on the basis of fluctuations of the pulse pressure vibrations and pulse wave amplitude while causing the pressure in the cuff to drop. However, there were the following shortcomings in this tonometry hemadynamometry method with such an oscillometric process.

That is, in the tonometry hemadynamometry method, as has been represented by an in-artery catheter method, the method for measuring the pressure applied to a blood vessel wall by determining one point of the artery of a patient is ideal. However, with the tonometry hemadynamometry method by the abovementioned oscillometric method, since the pressure fluctuations in an air bag of the cuff wound on the upper arm of a patient is detected and is used for measuring the blood pressure, a pulse pressure appears even in the in-cuff pressure which is higher than the maximum blood pressure or it is not clear to judge the minimum blood pressure.

With the tonometry hemadynamometry method with a conventional oscillometric process, this results from detecting the mean pulsation of the artery spreading in the range of the cuff, and the pulsation is such that the artery wall displacement of the brachial artery resulting from the heartbeat is propagated as displacements of the skin surface and further the displacement of the skin surface causes the air capacity in the air bag of the cuff to be changed, wherein this capacity change is detected as a pressure change in the cuff. Resultantly, the displacement quantity of the artery wall is converted to the pressure fluctuation in the cuff.

However, with such a method, since the displacement quantity of the artery wall is measured via air in the air bag of the cuff, it is not possible to faithfully obtain the artery wall displacement with only the pulse pressure wave obtained from inside the cuff because of receiving influences outside the body such as compression characteristics of air, damping characteristics thereof, etc.

This also means that although constituents of Korotoff's sounds which have higher frequency constituents than the pulse pressure waves are superposed with the pulse waveforms in a cuff pressure dropping process from the maximum blood pressure to the minimum blood pressure in the blood pressure measurement and must appear, fluctuations of higher frequency constituents such as Korotoff's sounds are not able to be propagated since air is used as a propagation medium in the in-cuff pulse pressure waveform in the oscillometric process, and resultantly it seems that such constituents do not appear.

That is, in a tonometry hemadynamometry method with a conventional oscillometric process, since a cuff is wound onto a long length of the brachial artery which is the portion to be measured of a patient and the pulse pressure vibrations are detected as pressure fluctuations in the cuff pressure, the artery pressure of the artery wall at one point which is ideal in the tonometry hemadynamometry method is not accurately reflected. Accordingly, a pulse pressure wave occurs in the cuff pressure which is more than the maximum blood pressure, and since the pulse pressure wave is propagated by using air as a medium, the frequency propagation is adversely influenced by the compression characteristics and damping characteristics of air, and a shortcoming is caused, whereby Korotoff's sound propagation is hindered.

The present invention was developed in view of solving these shortcomings, and it is therefore an object of the invention to provide a cuff for a sphygmomanometer which is able to accurately measure the blood pressure by directly measuring a local artery wall displacement.

DISCLOSURE OF THE INVENTION

In order to solve the object, the invention provides a cuff for a sphygmomanometer, which is attached to an appointed part of a patient and presses the artery by supplying air therein, and is characterized in having a hard curved plate retained between the inside and outside cloths mutually sewed together, an engaging fastener fixed at the outer surface of said outside cloth, an air bag fixed in the inner circumferential side of said inside cloth, and a photoelectric sensors installed between said inside and outside parts of said air bag.

Said photoelectric sensor may be composed of a reflection plate secured at the inside part of said air bag, and a light receiving element and a light emitting element secured at the outside part of said air bag.

Furthermore, said photoelectric sensor has a pair of light receiving and light emitting elements, wherein one of the abovementioned elements may be provided at the inside part of said air bag, and the other may be provided at the outside part of said air bag.

Said air bag may be composed of a transparent bag member and a latticed reinforcing fabric integrally incorporated in this bag member.

Since a cuff for a sphygmomanometer constructed above is provided with a hard curved plate retained between the inside and outside cloths mutually sewed together, an engaging fastener fixed at the outer surface of said outside cloth, an air bag fixed in the inner circumferential side of said inside cloth, and a photoelectric sensor installed between said inside and outside parts of said air bag, it is possible to directly measure the displacement quantity of a local artery wall by an photoelectric sensor and to obtain the maximum and minimum blood pressure values on the basis of this displacement quantity.

PREFERRED EMBODIMENT OF THE INVENTION

A preferred embodiment of the invention will be hereinafter concretely described with reference to the accompanying drawings.

Figure 1:
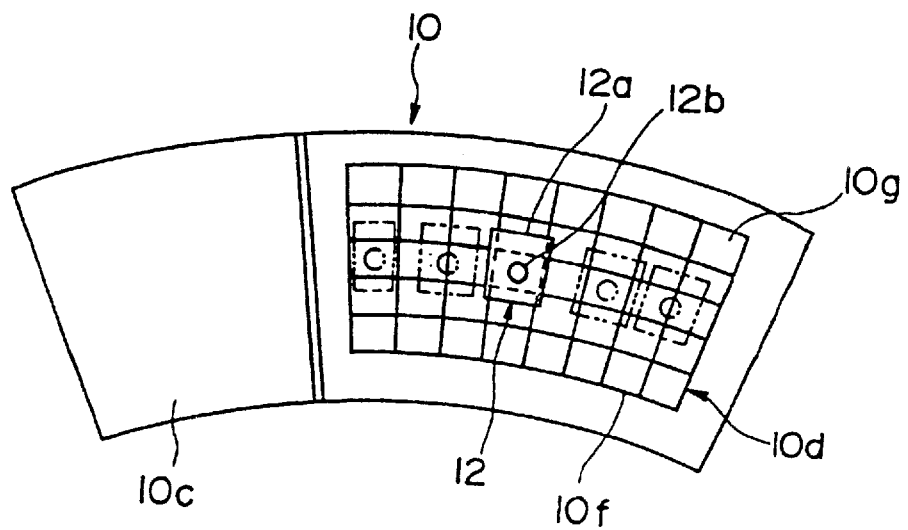
FIG. 1 is a developed view showing a preferred embodiment of a cuff for a sphygmomanometer according to the invention.
Figure 2:
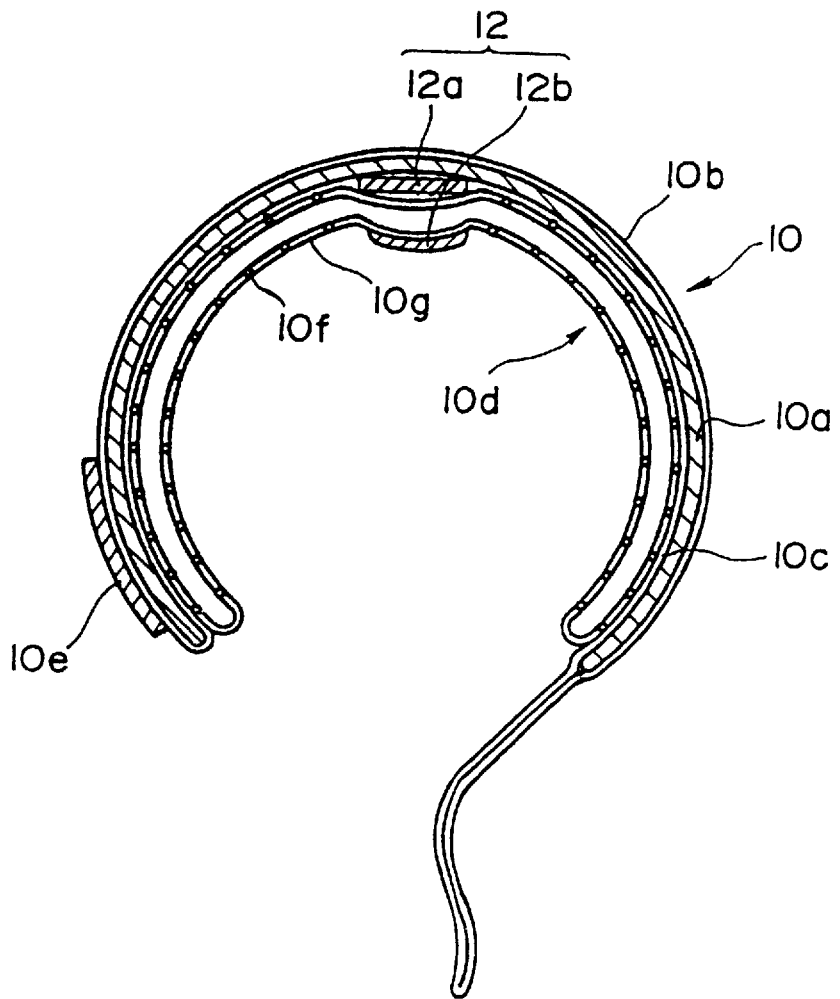
FIG. 2 is a cross-sectional view showing major parts of the cuff for a sphygmomanometer according to the invention.
Figure 3:
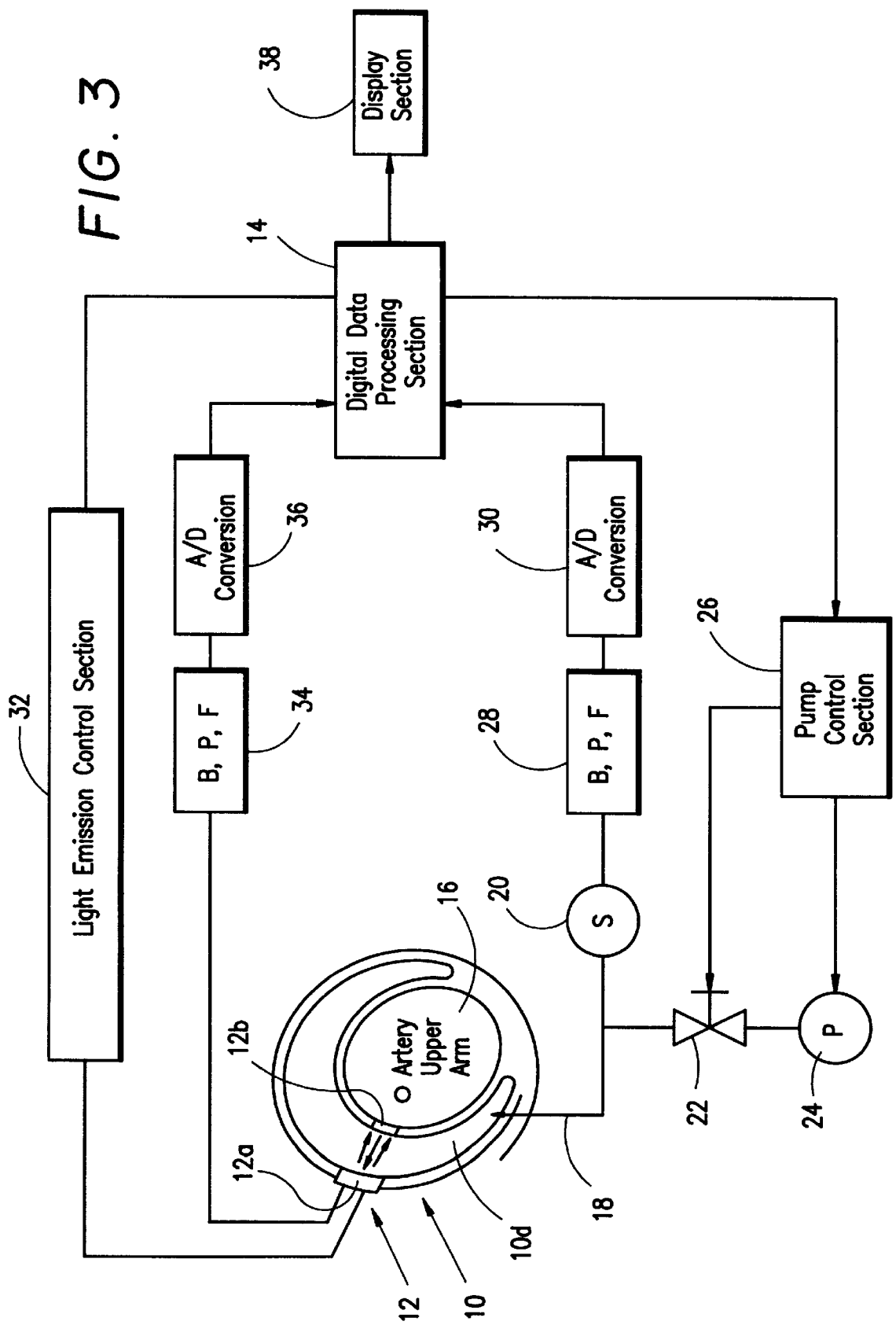
FIG. 3 is a block diagram showing a construction of a sphygmomanometer in which a cuff according to the invention is incorporated.

FIG. 1 and FIG. 2 show a preferred embodiment of a cuff for a sphygmomanometer according to the invention. FIG. 3 shows one example of a sphygmomanometer in which a cuff according to the invention is incorporated. A sphygmomanometer shown in the same drawing has a cuff 10, photoelectric sensor 12, and a digital data processing section 14. The cuff 10 is attached to an appointed part of a patient, concretely to the upper arm 16, the detail of which is shown in FIG. 1 and FIG. 2.

The cuff 10 shown in the same drawings is composed of a bendably deformable hard curved plate 10a made of a thin synthetic resin and formed to be arcuately curved, an outside cloth 10b which surrounds the outer periphery of said curved plate 10a, an inside cloth 10c sewed to the outside cloth 10b so that the same surrounds the inner periphery of said curved plate 10a, an air bag 10d secured inside the inside cloth 10c, and an engaging fastener 10e sewed to the outer periphery of the outside cloth 10b in order to stop the end parts of the inside cloth 10c.

The air bag 10d is composed of an enclosed transparent synthetic resin sheet made bag member 10g in which reinforcing fibers 10f are incorporated. Reinforcing fibers 10f are integrally incorporated in order to prevent elongation of the air bag 10g due to pulsations when the same is being compressed. When inflating the air member 10g by supplying air into the same air bag 10g via a tube 18 described later, it is possible to inflate the bag member 10g in proportion to the supplying quantity of air.

A tube 18 for supplying air is caused to communicate with and is connected to the inside of the bag member 10g. A pressure sensor 20 and a solenoid control valve 22 are connected to the outer end of the tube 18. And a pump 24 which is able to send out air is connected to the solenoid control valve 22, and both the solenoid control valve 22 and pump 24 are controlled by the pump controlling section 26.

Detection signals of the pressure sensor 20 are inputted into a digital data processing section 14 via a band pass filter 28 and an A/D converter 30. Control signals are sent from the digital data processing section 14 to the pump control section 26 on the basis of detection signals of the pressure sensor 20. The photoelectric sensor 12 is composed of a photocoupler 12a fixed at the outer surface of the outside party of the bag member 10g and a reflection plate 12b fixed at the outer surface of the inside part of the bag member 10g so that the same is opposite said photocoupler 12a.

Said photocoupler 12a is such that a light emitting diode is integrally assembled together with a phototransistor, and it is set so that the light emitted from the light emitting diode is reflected by the reflection plate 12b and is made incident into the phototransistor. The output size of the phototransistor may change according to the distance between the photocoupler 12a and the reflection plate 12b, whereby output signals are sent out in response to the displacement of the artery.

The light emitting diode of the photocoupler 12a is controlled to be turned on and off by a light emission control section 32 connected to the digital data processing section 14. The digital data processing section 14 is connected to the phototransistor of the photocoupler 12a via a band pass filter 34 and an A/D converter, whereby the detection signals of the transistor are digitalized and inputted into the processing section 14.

Furthermore, in this preferred embodiment, although a photocoupler 12a and a reflection plate 12b are disposed outside a bag member 10g since the bag member 10g is formed with a transparent synthetic resin sheet, the photocoupler 12a and reflection plate 12b may be disposed inside thereof if the bag member 10g is formed with a non-transparent synthetic resin sheet plate 10g.

Still furthermore, in a cuff 10 for a sphygmomanometer according to the invention, the photoelectric sensor 12 may employ not only a combination of a photocoupler 12a and a reflection plate 12b but also a combination of a light emitting diode and a photocoupler. In this case, these members may be disposed opposite each other at the inside and outside of the bag member 10g.

The digital data processing section 14 is composed of a so-called microcomputer which includes a CPU and a memory, and a display section 38 which displays the maximum and minimum blood pressure values is connected to this digital data processing section 14 via an interface.

When measuring the blood pressure, firstly, a cuff 10 is attached to the upper arm 16 of a patient. At this time, the cuff 10 is set so that the reflection plate 12 is positioned on the artery of the upper arm 16, and is fixed with the cloths 10b,10c engaged with the engaging fastener 10e.

Furthermore, in this case, in order to cause the reflection plate 12b to be positioned on the artery of the upper arm 16 of a patient without fail, for example, as shown by hypothetical lines in FIG. 1, if a plurality of optical range sensors 12 are disposed along the circumferential direction, it is possible to cause any one of the photoelectric sensors 12 to be positioned on the artery. In a case where a plurality of photoelectric sensors are employed, the one which outputs the largest output signal may be selected by comparing the output values of the respective sensors 12 when using a plurality of sensors 12.

Upon the completion of attaching a cuff 10, the preparation of blood pressure measurement is completed. Therefore, output signals are sent out from the digital data processing section 14 to the solenoid valve control section 22 thereby to cause the solenoid valve control valve 22 to be opened. And the solenoid control valve 22 is controlled on the basis of the detection signals of the pressure sensor 20, whereby a constant speed compression control by which the pressure inside the air bag 10d of the cuff 10 is increased at a constant speed is carried out.

At this time, since with a cuff 10 of the preferred embodiment, reinforcing fabric 10f are incorporated in the bag member 10g of the air bag 10g in a latticed state and a non-elastic curved plate 10a is caused to intervene at the outer circumference of the bag member 10d, the elongation and contraction of the bag member 10d are regulated, and the outward expansion of the bag member 10d is regulated by the curved plate 10a, whereby the photoelectric sensor 12 is prevented from being displaced.

Accordingly, the air bag 10d compresses the artery by inwardly displacing only the inside thereof with the outside of the air member 10g maintained as it is.

Detection signals sent from the photoelectric sensor 12 are taken into the digital data processing section 14 one after another. Since the output signals of this photoelectric sensor 12 includes parts corresponding to the expansion of the air bag 10d being compressed at a constant speed, the photoelectric volumetric pulse wave signals obtained by eliminating the parts corresponding to the constant speed compression are calculated in the digital data processing section 14, and the maximum blood pressure and maximum blood pressure are judged on these signals.

Figure 4:
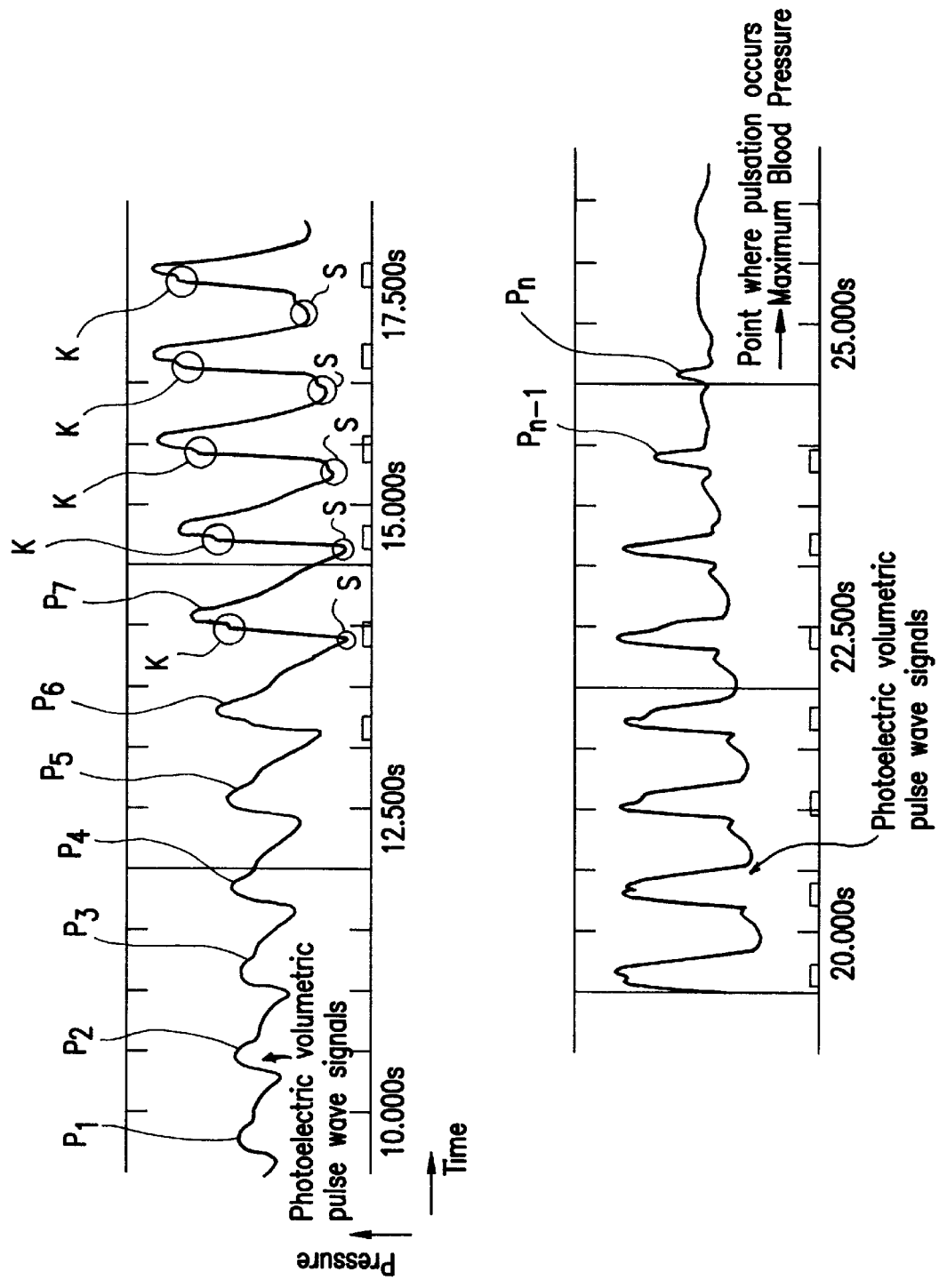
FIG. 4 is a wave form diagram showing one example of pulsation waves detected by the cuff for a sphygmomanometer shown in FIG. 1.

Those shown in FIG. 4 are one of the examples of photoelectric volumetric pulse wave signals. One example of a method for judging the maximum blood pressure and minimum blood pressure on the basis of these photoelectric volumetric pulse wave signals will be described below. For example, herein it is assumed that the photoelectric volumetric pulse wave signals P1, P2, P3, . . . Pn per pulse are extracted in a state shown in FIG. 4. It is judged whether or not any flat section exists in the respective photoelectric volumetric pulse wave signals P1, P2, P3, . . . Pn.

Herein, in the process of increasing pressure in the air bag 10d at a constant speed, in a case where the pressure in the air bag 10d is lower than the minimum blood pressure of a patient, the photoelectric volumetric pulse wave signals pulsate without being influenced by the pressure of the air bag 10d (Photoelectric volumetric pulse wave signals P1 to P6 in FIG. 4).

However, if the pressure in the air bag 10d becomes larger than the minimum blood pressure of a patient, a flat section s having no pressure fluctuation in the photoelectric volumetric pulse wave signals when the artery pressure is smaller than the pressure in the air bag 10d. Accordingly, this preferred embodiment is constructed so that a photoelectric volumetric pulse wave signal at which a flat section s occurs for the first time is detected, and the minimum blood pressure is judged when this photoelectric volumetric pulse wave signal P7 is detected.

In this minimum blood pressure judgement, for example, the pressure inside the air bag 10d at the moment when the photoelectric volumetric pulse wave signal P6 immediately before the photoelectric pulse wave signal P7 in which a flat section s occurred for the first time is extracted is made the minimum blood pressure or the mean value of the pressure inside the air bag 10d at the moment when the photoelectric pulse wave signal P7 and photoelectric volumetric pulse wave signal P6 are extracted is made the minimum blood pressure.

Furthermore, in the minimum blood pressure judgement in this case, as shown in FIG. 4, if the pressure inside the air bag 10d becomes larger than the minimum blood pressure of a patient, a high speed displacement part K corresponding to Korotoff's sounds occurs in the photoelectric volumetric pulse wave signals. Therefore, the photoelectric volumetric pulse wave signal in which this high speed displacement part K occurred for the first time is detected, and it is possible to obtain the minimum blood pressure value by a method similar to the case of the flat section s.

On the other hand, in the maximum blood pressure judgement, the moment when the photoelectric volumetric pulse wave signal disappears is judged as the maximum blood pressure. That is, if this pressure becomes larger than the maximum blood pressure when increasing the pressure inside the air bag 10d at a constant speed, the moment when no photoelectric volumetric pulse wave signal will be detected is judged as the maximum blood pressure of a patient, taking note of the artery pulsation being suppressed by the pressure and no displacement occurring at the photoelectric sensor 12.

According to a cuff for a sphygmomanometer of the preferred embodiment, which is constructed as shown above, since the cuff is provided with an air bag 10d fixed at the inner circumferential side of the inside cloth 10c and photoelectric sensors 12 secured inside and outside the air bag 10d, the displacement quantity of a local artery wall is able to be directly measured by photoelectric sensors 12, and the maximum and minimum blood pressure values can be obtained on the basis of this displacement quantity. Therefore, it is possible to accurately measure the blood pressure.

Industrial Feasibility

As concretely described in the abovementioned preferred embodiment, according to a cuff for a sphygmomanometer, since it is possible to directly measure the displacement quantity of a local artery wall by optical range sensors and to obtain the maximum and minimum blood pressure values on the basis of this displacement quantity, this cuff is suitable for a closed type sphygmomanometer which is able to obtain the maximum and minimum blood pressure values at a high accuracy.

What is claimed is:

1. A cuff for a sphygmomanometer adapted for attachment to an appointed part of a patient and adapted for compression of an artery, comprising a hard curved plate retained between an inside cloth and outside cloth sewed to each other, an engaging fastener fixed on an outer surface of said outside cloth, an air bag fixed at an inner circumferential side of said inside cloth and having an inside and an outside, and a photoelectric sensor installed between the inside and outside of said air bag, wherein said photoelectric sensor includes a reflection plate secured at the inside part of said air bag and a light receiving element and a light emitting element which are provided at the outside part of said air bag.

2. A cuff for a sphygmomanometer as set forth in claim 1, wherein said photoelectric sensor includes a light receiving element and light emitting element, one of which is provided at the inside part of said air bag, and the other of which is provided at the outside part of said air bag.

3. A cuff for a sphygmomanometer as set forth in claim 1, wherein said air bag includes a transparent bag member and a latticed reinforcing fabric integrally incorporated in the air bag.

4. A cuff for a sphygmomanometer adapted for attachment to an appointed part of a patient and adapted for compression of an artery, comprising a hard curved plate retained between an inside cloth and outside cloth sewed to each other, an engaging fastener fixed on an outer surface of said outside cloth, an air bag fixed at an inner circumferential side of said inside cloth and having an inside and an outside, and a photoelectric sensor installed between the inside and outside of said air bag wherein said photoelectric sensor includes first and second elements installed between the inside and the outside of said air bag, respectively, wherein one of said elements is a light emitting element, and the other of said elements is a reflection plate or a light receiving element.

5. A cuff for a sphygmomanometer adapted for attachment to an appointed part of a patient and adapted for compression of an artery, comprising a hard curved plate retained between an inside cloth and outside cloth sewed to each other, an engaging fastener fixed on an outer surface of said outside cloth, an air bag fixed at an inner circumferential side of said inside cloth and having an inside and an outside, and a photoelectric sensor installed between the inside and outside of said air bag, wherein said air bag includes a transparent bag member and a latticed reinforcing fabric integrally incorporated in the air bag.

* * * * *